US007019022B2

(12) United States Patent
Beaulieu et al.

(10) Patent No.: US 7,019,022 B2
(45) Date of Patent: Mar. 28, 2006

(54) SUBSTITUTED TETRAHYDROCARBAZOLE AND CYCLOPENTANOINDOLE DERIVATIVES

(75) Inventors: Christian Beaulieu, Laval (CA); Daniel Guay, Notre Dam de I'lle Perrot (CA); Zhaoyin Wang, Kirkland (CA); Robert Zamboni, Pointe Claire (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 11/007,009

(22) Filed: Dec. 8, 2004

(65) Prior Publication Data

US 2005/0154044 A1 Jul. 14, 2005

Related U.S. Application Data

(60) Provisional application No. 60/530,298, filed on Dec. 15, 2003.

(51) Int. Cl.
*A61K 31/40* (2006.01)
*C07D 209/88* (2006.01)

(52) U.S. Cl. ...................................... 514/411; 548/443

(58) Field of Classification Search ................ 514/411; 548/443

See application file for complete search history.

(56) References Cited

U.S. PATENT DOCUMENTS 4,808,608 A 2/1989 Guindon et al.
6,410,583 B1 6/2002 Labelle et al.
2003/0158246 A1 8/2003 Berthelette et al.

FOREIGN PATENT DOCUMENTS

WO WO 2004/103970 A1 12/2004
WO WO 2005/013985 A1 2/2005

*Primary Examiner*—Kamal A. Saeed
(74) *Attorney, Agent, or Firm*—Mollie M. Yang; David L. Rose

(57) ABSTRACT

The present invention provides substituted tetrahydrocarbazole and cyclopentanoindole derivatives as antagonists of DP receptor, and as such are useful for the treatment of prostaglandin D2 mediated diseases such as rhinitis, asthma and nasal congestion.

11 Claims, No Drawings

SUBSTITUTED TETRAHYDROCARBAZOLE AND CYCLOPENTANOINDOLE DERIVATIVES

CROSS REFERENCE TO RELATED APPLICATIONS

This application claims the benefit of U.S. Provisional application No. 60/530,298, filed Dec. 15, 2003.

BACKGROUND OF THE INVENTION

The present invention relates to compounds and methods for treating prostaglandin mediated diseases, and certain pharmaceutical compositions thereof. More particularly, the compounds of the invention are structurally different from steroids, antihistamines or adrenergic agonists, and are antagonists of the nasal and pulmonary congestion effects of D-type prostaglandins.

Two review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137–154 and Journal of Lipid Mediators and Cell Signalling, 1996, 14, 83–87. An article from T. Tsuri et al. published in 1997 in Journal of Medicinal Chemistry, vol 40, pp. 3504–3507 states that "PGD2 is considered to be an important mediator in various allergic diseases such allergic rhinitis, atopic asthma, allergic conjunctivitis and atopic dermatitis." More recently, an article by Matsuoka et al. in *Science* (2000), 287: 2013–7, describes PGD2 as being a key mediator in allergic asthma. In addition, patents such as U.S. Pat. No. 4,808,608 refer to prostaglandin antagonists as useful in the treatment of allergic diseases, and explicitly allergic asthma. PGD2 antagonists are described in, for example, European Patent Application 837,052 and PCT Application WO98/25919, as well as WO99/62555.

SUMMARY OF THE INVENTION

The present invention provides novel compounds which are prostaglandin receptor antagonists; more particularly, they are prostaglandin D2 receptor (DP receptor) antagonists. Compounds of the present invention are useful for the treatment of various prostaglandin-mediated diseases and disorders; accordingly the present invention provides a method for the treatment of prostaglandin-mediated diseases using the novel compounds described herein, as well as pharmaceutical compositions containing them.

DETAILED DESCRIPTION OF THE INVENTION

The present invention provides compounds of the formula I:

I

F, $R^{4a}$, $R^{4b}$, $)_n$, $CO_2H$, N, $H_3C$, S, O, O, $R^3$, $R^1$, $R^2$ and pharmaceutically acceptable salts thereof, wherein n is 0 or 1; $R^1$ is hydrogen or halogen; $R^2$ is halogen, cyano, $C_{1-3}$alkylsulfonyl or trifluoromethyl; $R^3$ is $C_{1-3}$alkyl optionally substituted with 1–5 halogen atoms; and $R^{4a}$ and $R^{4b}$ are each hydrogen or one is hydrogen and the other is hydroxy, or both together represent oxo; with the proviso that when $R^1$ is hydrogen, $R^2$ is not 4-chloro.

In one embodiment of formula I are compounds wherein $R^{4a}$ and $R^{4b}$ are each hydrogen.

In a second embodiment of formula I are compounds wherein $R^1$ is hydrogen and $R^2$ is trifluoromethyl.

In a third embodiment of formula I are compounds wherein $R^3$ is methyl.

In a fourth embodiment of formula I are compounds wherein $R^1$ and $R^2$ are independently a halogen atom.

In a fifth embodiment of formula I are compounds wherein n is 1.

In a sixth embodiment of formula I are compounds wherein n is 1, $R^3$ is $CH_3$, and $R^{4a}$ and $R^{4b}$ are each hydrogen.

In a seventh embodiment of formula I are compounds wherein n is 1, $R^3$ is $CH_2F$ or $CHF_2$, and $R^{4a}$ and $R^{4b}$ are each hydrogen.

In an eighth embodiment of formula I are compounds wherein n is 1, $R^1$ is hydrogen, $R^3$ is methyl, $R^{4a}$ and $R^{4b}$ are each hydrogen, and $R^2$ is 4-cyano, 4-methanesulfonyl or 4-trifluoromethyl.

The present invention further provides a compound selected from:

((1R)-6-fluoro-8-(methylsulfonyl)-9-{(1S)-1-[4-(trifluoromethyl)phenyl]ethyl}-2,3,4,9-tetrahydro-1H-carbazol-1-yl)acetic acid;

[(1R)-9-[(1S)-1-(3,4-dichlorophenyl)ethyl]-6-fluoro-8-(methylsulfonyl)-2,3,4,9-tetrahydro-1H-carbazol-1-yl]acetic acid;

{(1R)-6-fluoro-8-(methylsulfonyl)-9-[(1S)-1-phenylethyl]-2,3,4,9-tetrahydro-1H-carbazol-1-yl}acetic acid;

[(1R)-6-fluoro-9-[(1S)-1-(4-fluorophenyl)ethyl]-8-(methylsulfonyl)-2,3,4,9-tetrahydro-1H-carbazol-1-yl]acetic acid;

[(1R)-9-[(1S)-1-(4-chloro-3-fluorophenyl)ethyl]-6-fluoro-8-(methylsulfonyl)-2,3,4,9-tetrahydro-1H-carbazol-1-yl] acetic acid;

[(1R)-9-[(1S)-1-(3-chlorophenyl)ethyl]-6-fluoro-8-(methylsulfonyl)-2,3,4,9-tetrahydro-1H-carbazol-1-yl]acetic acid;

[(1R)-9-[(1S)-1-(4-chloro-2-fluorophenyl)ethyl]-6-fluoro-8-(methylsulfonyl)-2,3,4,9-tetrahydro-1H-carbazol-1-yl] acetic acid;

[(1R)-9-[(1S)-1-(4-bromophenyl)ethyl]-6-fluoro-8-(methylsulfonyl)-2,3,4,9-tetrahydro-1H-carbazol-1-yl]acetic acid;

[(1R)-9-[(1S)-1-(4-cyanophenyl)ethyl]-6-fluoro-8-(methylsulfonyl)-2,3,4,9-tetrahydro-1H-carbazol-1-yl]acetic acid; and ((1R)-6-fluoro-8-(methylsulfonyl)-9-{((1S)-1-[4-(methylsulfonyl)phenyl]ethyl}-2,3,4,9-tetrahydro-1H-carbazol-1-yl)acetic acid; and pharmaceutically acceptable salts therof.

Compounds of formula I are selective antagonists of the DP receptor with 10 fold or greater affinity for the DP versus other prostanoid receptor (TP, EP1, EP2, EP3, EP4, FP, IP) and the PGD2 receptor CRTH2 (also known as DP2).

In another aspect of the present invention there is provided pharmaceutical compositions comprising a compound of formula I, and a pharmaceutically acceptable carrier.

In one embodiment, the pharmaceutical compositions further comprises a second active ingredient selected from an antihistamine, a leukotriene antagonist, leukotriene biosynthesis inhibitor, prostaglandin receptor antagonists or biosynthesis inhibitors, corticosteroids, cytokine modulators, anti-IgE, anti-cholinergics or NSAIDS.

In another aspect of the present invention there is provided a method for the treatment or prevention of prostaglandin D2 mediated diseases which comprises administering to a patient in need of treatment a therapeutically effective amount of a compound of formula I.

In one embodiment of the invention is a method of treating or preventing a prostaglandin D2 mediated disease comprising administering to a mammalian patient in need of such treatment a compound of formula I in an amount which is effective for treating or preventing a prostaglandin D2 mediated disease, wherein the prostaglandin mediated disease is nasal congestion, rhinitis including seasonal allergic rhinitis and perennial allergic rhinitis, and asthma including allergic asthma.

In another embodiment of the present invention is a method for the treatment of nasal congestion in a patient in need of such treatment which comprises administering to said patient a therapeutically effective amount of a compound of formula I.

In yet another embodiment of the present invention is a method for the treatment of asthma, including allergic asthma, in a patient in need of such treatment which comprises administering to said patient a therapeutically effective amount of a compound of formula I.

In yet another embodiment of the present invention is a method for the treatment of allergic rhinitis (seasonal and perennial) in a patient in need of such treatment which comprises administering to said patient a therapeutically effective amount of a compound of formula I.

Another aspect of the present invention provides a method for preventing or reducing niacin-induced flushing in a mammal in need of such treatment comprising administering to said mammal a therapeutically effective amount of a compound of formula I.

Another aspect of the present invention provides the use of a compound of formula I or a pharmaceutically acceptable salt thereof, for the manufacture of a medicament for the treatment or prevention of conditions for which the administration of a DP receptor antagonist is indicated.

As used herein, the term "halogen" includes fluorine, chlorine, bromine and iodine. The term "alkyl" includes linear and branched carbon chains having the indicated range of carbon atoms.

The numbering of the core tricyclic ring systems of formula I is as shown below:

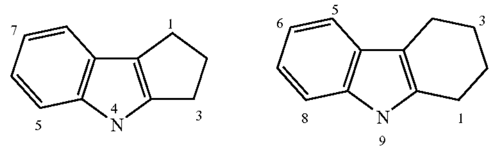

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethyl-aminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I are meant to also include the pharmaceutically acceptable salts.

Utilities

Compounds of formula I are antagonists of prostaglandin D2. The ability of compounds of formula I to interact with prostaglandin D2 receptor makes them useful for preventing or reversing undesirable symptoms caused by prostaglandins in a mammalian, especially human subject. The antagonism of the actions of prostaglandin D2 indicates that the compounds and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of cancer. Compounds of formula I may also be of use in the treatment and/or prevention prostaglandin D2 mediated proliferation disorders such as may occur in diabetic retinopathy and tumor angiogenesis. Compounds of formula I may also inhibit prostanoid-induced smooth muscle contraction by antagonizing contractile prostanoids or mimicking relaxing prostanoids and hence may be used in the treatment of dysmenorrhea, premature labor and eosinophil related disorders.

Accordingly, another aspect of the invention provides a method of treating or preventing a prostaglandin D2 mediated disease comprising administering to a mammalian patient in need of such treatment a compound of formula I in an amount which is effective for treating or preventing said prostaglandin D2 mediated disease. Prostaglandin D2 mediated diseases include, but are not limited to, allergic rhinitis, nasal congestion, rhinorrhea, perennial rhinitis, nasal inflammation, asthma including allergic asthma, chronic obstructive pulmonary diseases and other forms of lung inflammation; pulmonary hypotension; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases, such as for example atherosclerosis; congestive heart failure; diseases or conditions requiring a treatment of anti-coagulation such as post-injury or post surgery treatment; rheumatoid arthritis and other inflammatory diseases; gangrene; Raynaud's disease; mucus secretion disorders including cytoprotection; pain and migraine; diseases requiring control of bone formation and resorption such as for example osteoporosis; shock; thermal regulation including fever; rejection in organ transplant and by-pass surgery, and immune disorders or conditions in which immunoregulation is desirable. More particularly the disease to be treated is one mediated by prostaglandin D2 such as nasal congestion, allergic rhinitis, pulmonary congestion, and asthma including allergic asthma.

In addition, compounds of formula I are useful for alleviating flushing caused by niacin or nicotinic acid (pyridine-3-carboxylic acid), a drug commonly known for its effect in elevating serum levels of high density lipoproteins (HDL). Niacin is frequently associated with cutaneous vasodilation, sometimes called flushing. This side effect is caused by the nicotinic acid-induced release of prostaglandin D2 in the skin and is so severe that many patients discontinue nicotinic acid treatment. Consequently, in another aspect the present invention provides for a method for preventing or reducing niacin-induced flushing in a mammal in need of such treatment comprising administering to said mammal a therapeutically effective amount of a compound of formula I. In this aspect, niacin and the compound of formula I may be administered together in unit dosage form or in separate dosage forms, or the compounds may be administered sequentially.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of prostaglandin mediated diseases, compound of formula I may be co-administered with other therapeutic agents. Thus in another aspect the present invention provides pharmaceutical compositions for treating prostaglandin D2 mediated diseases or conditions comprising a therapeutically effective amount of a compound of formula I and one or more other therapeutic agents. Suitable therapeutic agents for combination therapy with a compound of formula I include: (1) a prostaglandin receptor antagonist; (2) a corticosteroid such as triamcinolone acetonide; (3) a β-agonist such as salmeterol, formoterol, terbutaline, metaproterenol, albuterol and the like; (4) a leukotriene modifier, such as a leukotriene antagonist or a lipooxygenase inhibitor such as montelukast, zafirlukast, pranlukast, or zileuton; (5) an antihistamine (histamine H1 antagonist) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, norastemizole, terfenadine, loratadine, cetirizine, levocetirizine, fexofenadine, desloratadine, and the like; (6) a decongestant including phenylephrine, phenylpropanolamine, pseudophedrine, oxymetazoline, ephinephrine, naphazoline, xylo-metazoline, propylhexedrine, or levo-desoxyephedrine; (7) an antiitussive including codeine, hydrocodone, caramiphen, carbetapentane, or dextramethorphan; (8) another prostaglandin ligand including prostaglandin F agonist such as latanoprost; misoprostol, enprostil, rioprostil, ornoprostol or rosaprostol; (9) a diuretic; (10) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors such as celecoxib and rofecoxib, etoricoxib and valdecoxib; (12) inhibitors of phosphodiesterase type IV (PDE-IV) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) antidiabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2 or BK1) antagonists, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206.

In addition, the invention encompasses a method of treating prostaglandin D2 mediated diseases or conditions comprising: administering to a patient in need of such treatment a therapeutically effective amount of the compound of formula I, co-administered with one or more of such ingredients as listed immediately above. The amounts of active ingredients may be those commonly used for each active ingredient when it is administered alone, or in some instances the combination of active ingredients may result in lower dosage for one or more of the active ingredients. The present invention further provides a pharmaceutical composition comprising a therapeutically effective amount of niacin and a therapeutically effective amount of a compound of formula I or a pharmaceutically acceptable salt thereof, and a pharmaceutically acceptable carrier. The present invention also provides for the use of a compound of formula I or a pharmaceutically acceptable salt thereof and niacin in the manufacture of a medicament for elevating serum high density lipoprotein while reducin niacin-induced flushing.

Abbreviations Used

Ac=acetyl; AcOH=acetic acid; Bu=butyl; DAST=(diethylamino)sulfur trifluoride; DDQ=2,3-dichloro-5,6-dicyano-1,4-benzoquinone; DMF=dimethylformamide; DMSO=dimethylsulfoxide; EDCI=1-(3-dimethylaminopropyl)-3-ethylcarbodiimide hydrochloride; eq.=equivalent(s); Et=ethyl; EtOAc=ethyl acetate; EtOH=ethanol; HPLC=high pressure liquid chromatography; iPrOH=Isopropyl alcohol; Me=methyl; MeOH=methanol; TBAF=tetrabutylammonium fluoride; TBDMS=t-butyldimethylsilyl; THF=tetrahydrofuran.

Methods of Synthesis

Compounds of Formula I of the present invention can be prepared according to the synthetic routes outlined in Schemes 1 to 11 and by following the methods described herein. Scheme 1 depicts the preparation of intermediates of Formula IV from phenyl hydrazine II and cycloalkanone III (where R is ester group such as an alkyl group) under Fisher Indole or similar conditions Scheme 1

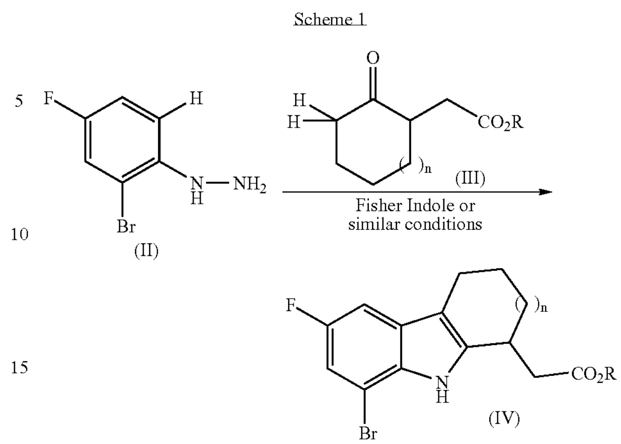

Scheme 2 depicts the preparation of compounds of Formula III from silyl enol ether IIIa or enamine IIIb. Reaction of an appropriate electrophile such as Y—$CH_2CO_2R$ (wherein Y represents a halogen or a leaving group) in the presence of a base such as an alkyl lithium or a Lewis acid such as silver trifluoroacetate with the silyl enol ether IIIa gives the cycloalkanone III. The compound of formula III may alternatively be prepared from the addition of Y—$CH_2CO_2R$ on an appropriately substituted enamine IIIb under Stork Enamine or similar conditions.

Scheme 2

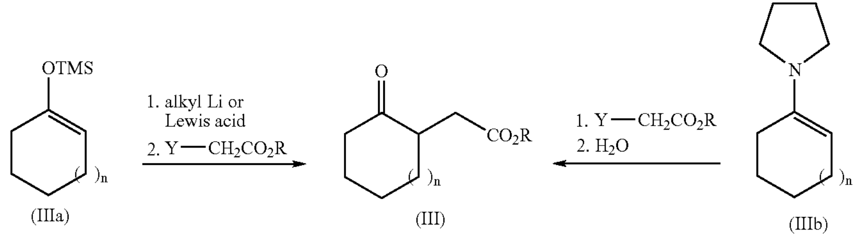

Scheme 3 depicts the preparation of compounds of Formula I from the chiral bromoindole IVa. The racemic mixture of IV may be resolved using conventional techniques; for example by resolution of IV by chiral HPLC, by enantioselective enzymatic transformations using enzymes such as esterases, or by using optically active resolving agents. Alkylation of IVa with an electrophile such as the benzyl compound V in the presence of a base and in a suitable solvent such as DMF gives N-alkylated indole VII. Coupling of VII with a methanesulfinate such as sodium methanesulfinate in the presence of Cu(I) salts leads to compounds of formula I, following ester hydrolysis. The bromoindole acid (VII, R═H) may alternatively first react with a suitable metallation agent, such as n-BuLi, followed by trapping with an electrophile such as methyl disulfide to give the corresponding methyl sulfide, which upon oxidation with for example hydrogen peroxide/sodium tungstate provides compound IA. The steps of alkylation of the bromoindole IVa followed by sulfonylation may also be reversed; thus sulfonylation of the bromoindole IVa provides the compound VI, which is alkylated using similar conditions as described before or by using Mitsunobu reaction conditions with benzyl alcohol VIII to provide compound of formula Ia following ester hydrolysis.

Scheme 3

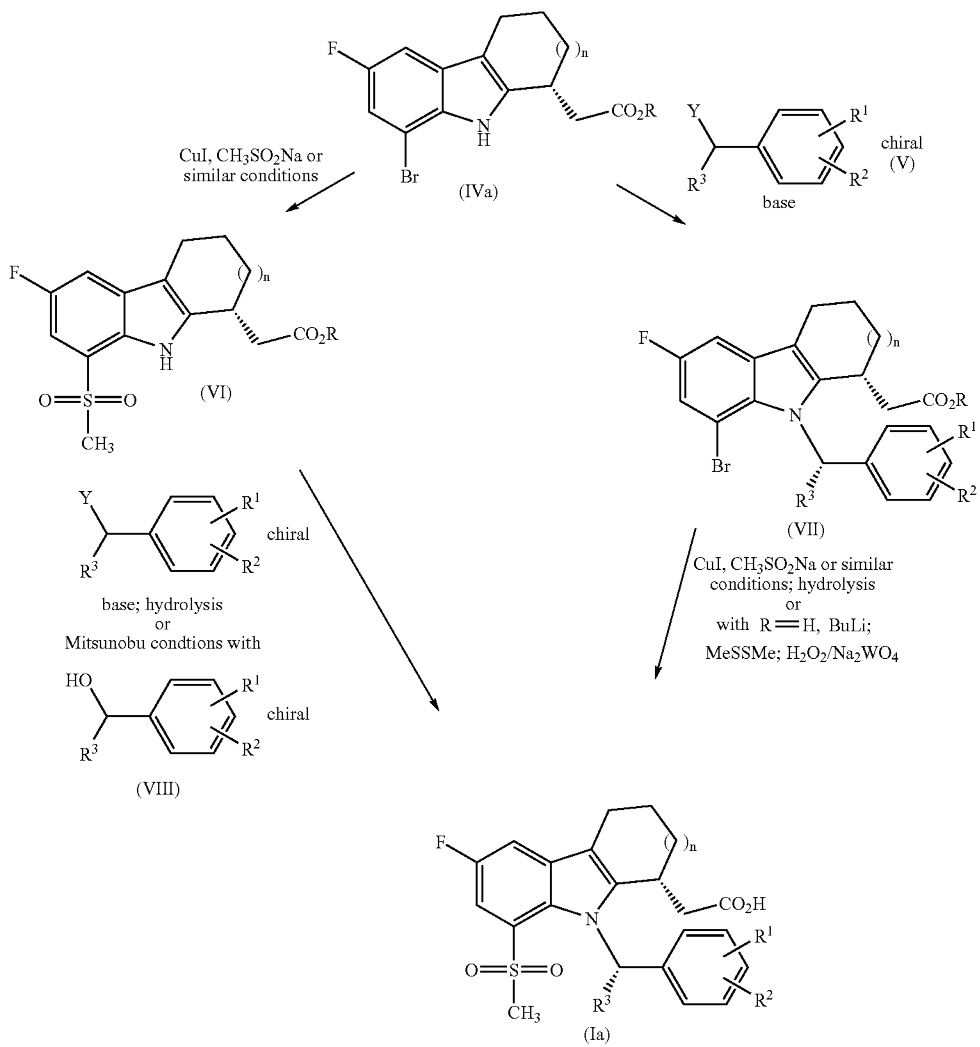

Scheme 4 depicts the preparation of compounds of Formula I from the chiral sulfone IXa. The racemic sulfone IX is prepared from coupling of bromide IV with a methanesulfinate such as sodium methanesulfinate in the presence of Cu(I) salts, which is then resolved by chiral HPLC, enantioselective enzymatic hydrolysis or by chiral resolving agents to afford the chiral sulfone IXa. Alkylation of IXa with an electrophile or by using Mitsunobu reaction condition as described in Scheme 3 provides compound of Formula Ia following ester hydrolysis.

Scheme 4

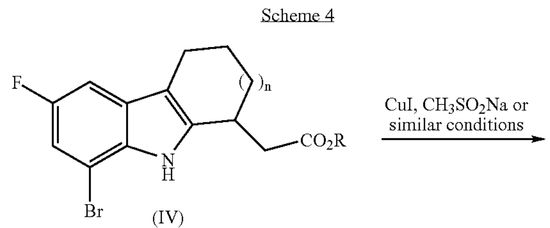

-continued

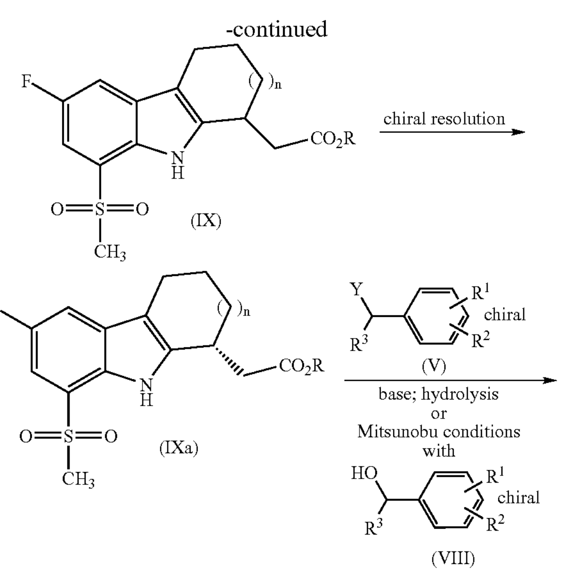

-continued

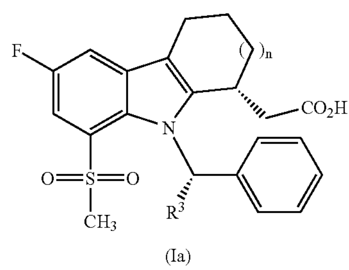

(Ia)

Alternatively, the racemic sulfone IX could be used for the alkylation step as depict in Scheme 5 to prepare the ester X (R═Me or Et) as a mixture of 2 diastereomers. Diastereoselective hydrolysis of X using LiOH at 0° C. affords the compound of Formula Ia and the ester Xa as single diastereomers which are easily separable by conventional separation techniques.

Scheme 5

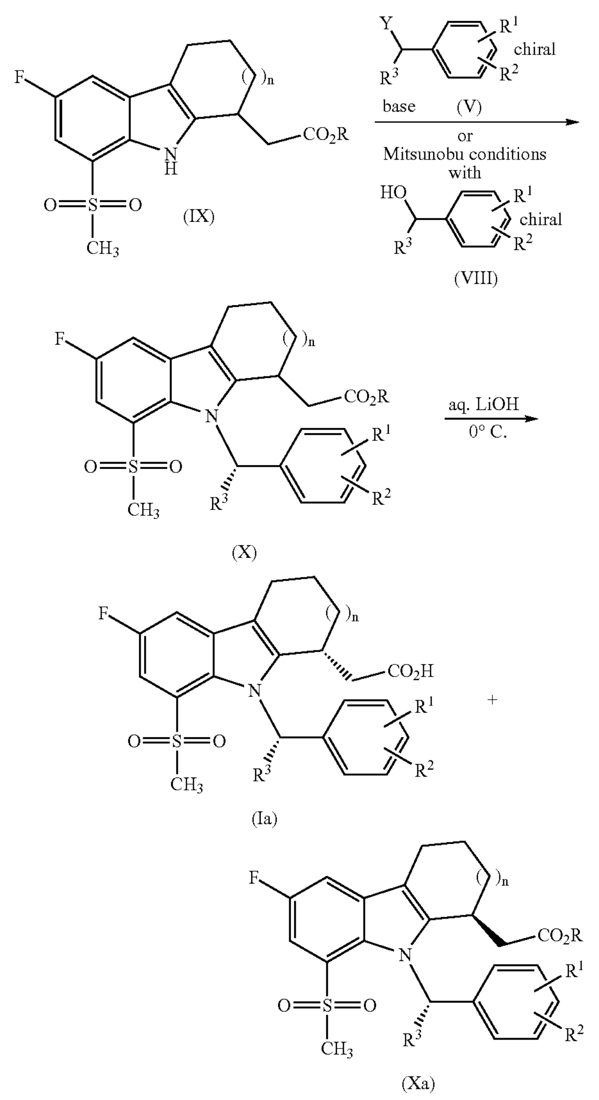

The chiral sulfone IXb could also be prepared from Ia by hydrogenolysis reaction using palladium on charcoal in MeOH to afford the methyl ester IXb as depict in Scheme 6.

Scheme 6

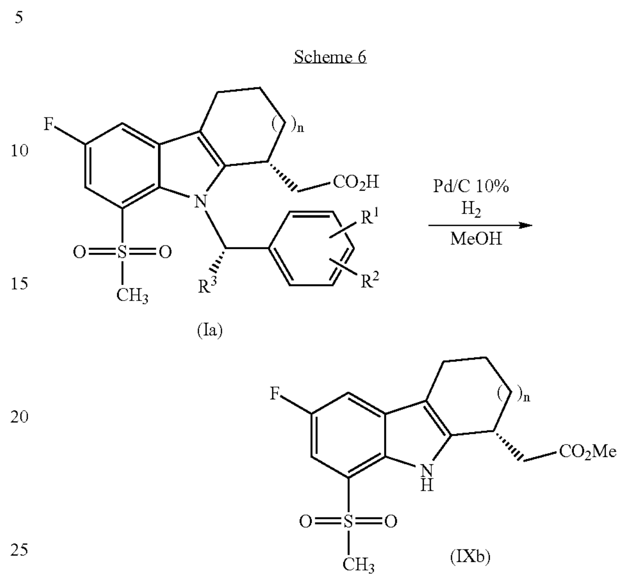

Compound Ib may be prepared from IXa, by oxidation using a suitable oxidant such as DDQ in THF, followed by alkylation step and by hydrolysis as illustrated in Scheme 3.

Scheme 7

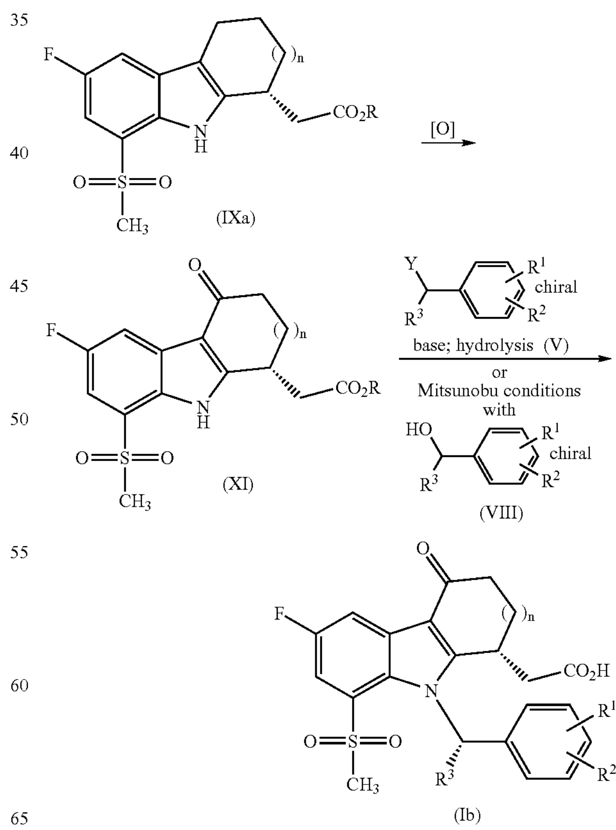

Chiral alcohol VIII may be prepared from the corresponding ketone XII by enantioselective reduction with a number of chiral reducing agents such as the combination of $BH_3.5Me_2$ with (Me)—CBS.

Scheme 8

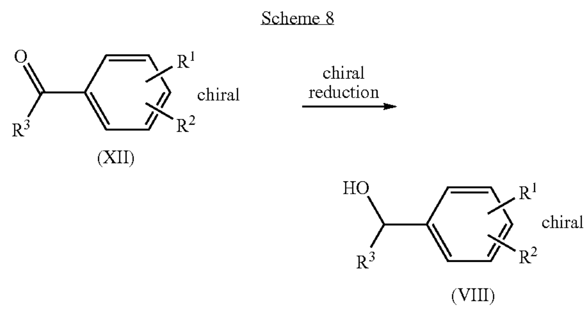

Compounds of Formula Ic and Id may be prepared by the sequence illustrated in Scheme 9. Asymmetric dihydroxylation of XIII using condition such as Sharpless dihydroxylation afford the diol XIV which is selectively protected with a protective group such as TBDMS to afford XV. Compound XVI is prepared by Mitsunobu reaction type between indole IX and alcohol XV and then deprotected with reagent such as TBAF. Compound of Formula Ic is then obtained following the conversion of XVII to the corresponding mesylate and treatment of the latter with fluorinating agent such as $NEt_3.3HF$ and finally by ester hydrolysis. Compound of Formula Id is prepared from XVII following oxidation, fluorination with reagent such as DAST and ester hydrolysis.

Scheme 9

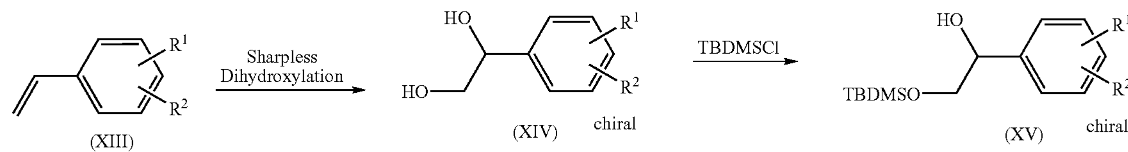

(IX) Mitsunobu condition with XV → (XVI) TBAF →

(XVII) 1. MsCl, $NEt_3$ 2. $NEt_3$•3HF 3. hydrolysis → (Ic)

(XVII) 1. [O] 2. DAST 3. hydrolysis → (Id)

Compounds of Formula Ie may be may be prepared by the sequence illustrated in Scheme 10. Oxidation of XVII using for example Dess-Martin or Swem protocols followed by aqueous hypochlorite treatment affords the corresponding carboxylate which may be treated with cyanuric acid or a 2-fluoropyridinium reagent or thionyl chloride and $KHF_2$ to give the acyl fluoride XVIII. Compound of formula Ie may then be obtained by treatment of XVIII with a fluorinating agent such as $SF_4$/HF or $F_3S—N(CH_2CH_2OMe)_2$ followed by ester hydrolysis.

Scheme 10

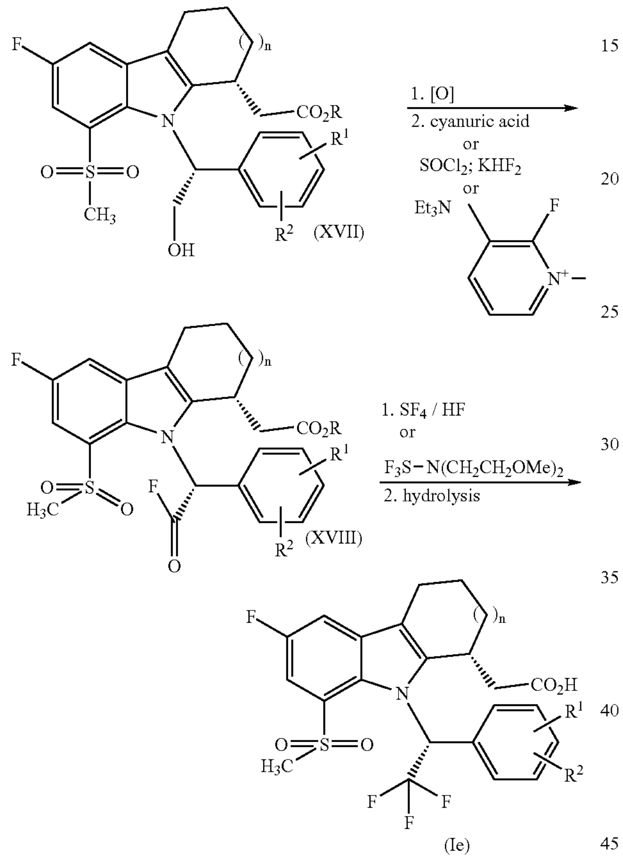

Scheme 11 depicts the preparation of compounds of Formula If and Ig from the chiral indole IXb. Oxidation using DDQ in toluene and acetic acid followed by treatment with aqueous bicarbonate affords XIX as a mixture of diastereomers. Coupling with chiral alcohol VIII under Mitsunobu conditions gives a separable mixture of isomers XXa and XXb. Final hydrolysis produces compounds of Formula If and Ig.

Scheme 11

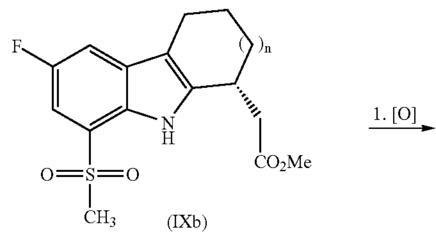

-continued

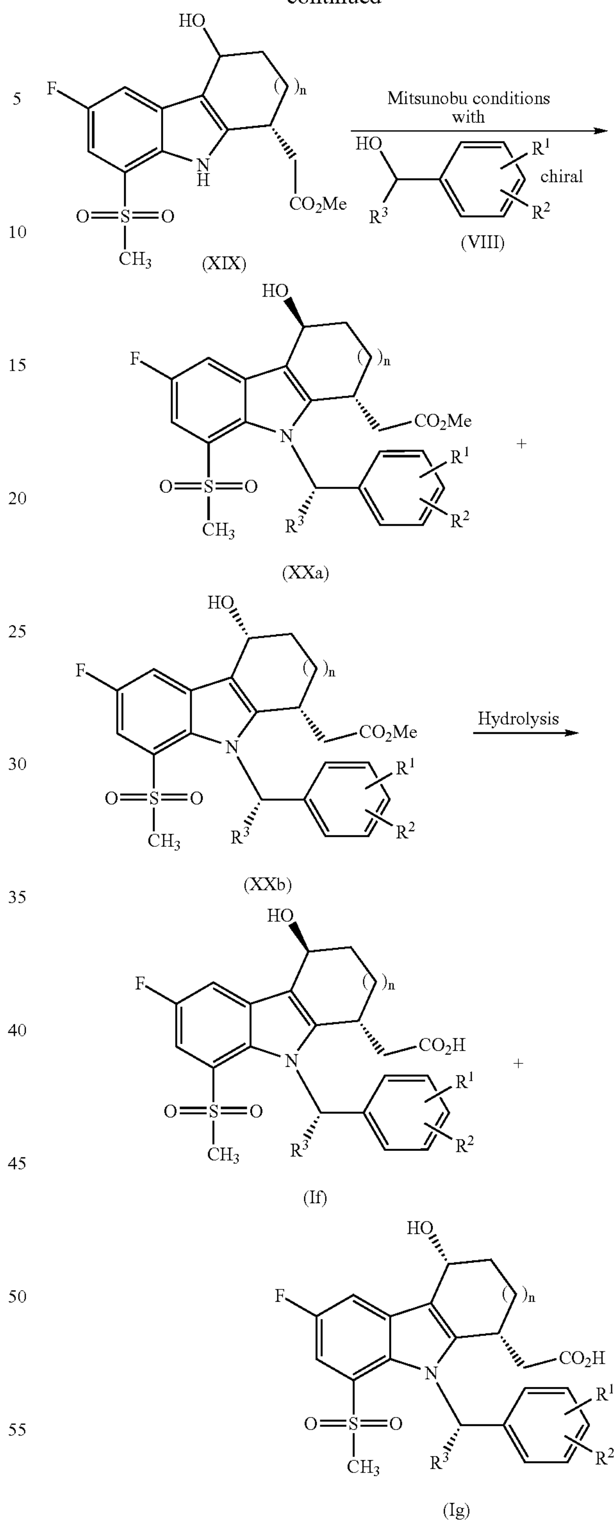

Assays for Determining Biological Activity

Compounds of formula I can be tested using the following assays to determine their prostanoid antagonist or agonist activity in vitro and in vivo and their selectivity. The prostaglandin receptor activities demonstrated are DP, $EP_1$, $EP_2$, $EP_3$, $EP_4$, FP, IP, TP and CRTH2.

Stable Expression of Prostanoid Receptors in the Human Embryonic Kidney (HEK) 293(ebna) Cell Line Prostanoid receptor and CRTH2 cDNAs corresponding to full length coding sequences are subcloned into the appropriate sites of mammalian expression vectors and transfected into HEK 293(ebna) cells. HEK 293(ebna) cells expressing the individual cDNAs are grown under selection and individual colonies are isolated after 2–3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP, CRTH2 and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 μM of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 μM RO-20174 (phosphodiesterase type IV inhibitor, available from Biomol) and, in the case of the $EP_3$ inhibition assay only, 15 μM forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both $K_B$ and slope values are calculated.

Prevention of PGD2 or Allergen Induced Nasal Congestion in Allergic Sheep

Animal preparation: Healthy adult sheeps (18–50 kg) are used. These animals are selected on the basis of a natural positive skin reaction to an intradermal injection of *Ascaris suum* extract.

Measurements of nasal congestion: The experiment is performed on conscious animals. They are restained in a cart in a prone position with their heads immobilized. Nasal airway resistance (NAR) is measured using a modified mask rhinometry technique. A topical anaesthesia (2% lidocaine) is applied to the nasal passage for the insertion of a nasotracheal tube. The maximal end of the tube is connected to a pneumotachograph and a flow and pressure signal is recorded on an oscilloscope linked to a computer for on-line calculation of NAR. Nasal provocation is performed by the administration of an aerosolized solution (10 puffs/nostril). Changes in the NAR congestion are recorded prior to and for 60–120 minutes post-challenge.

Prevention of PGD2 and Allergen Induced Nasal Obstruction in Cynomolgus Monkey

Animal preparation: Healthy adult male cynomologus monkeys (4–10 kg) are used. These animals are selected on the basis of a natural positive skin reaction to an intradermal injection of *Ascaris suum* extract. Before each experiment, the monkey selected for a study is fasted overnight with water provided at libitum. The next morning, the animal is sedated with ketamine (10–15 mg/kg i.m.) before being removed from its home cage. It is placed on a heated table (36° C.) and injected with a bolus dose (5–12 mg/kg i.v.) of propofol. The animal is intubated with a cuffed endotracheal tube (4–6 mm I.D.) and anaesthesia is maintained via a continuous intravenous infusion of propofol (25–30 mg/kg/h). Vital signs (heart rate, blood pressure, respiratory rate, body temperature) are monitored throughout the experiment.

Measurements of nasal congestion: A measurement of the animal respiratory resistance is taken via a pneumotachograph connected to the endotracheal tube to ensure that it is normal. An Ecovision accoustic rhinometer is used to evaluate nasal congestion. This technique gives a non-invasive 2D echogram of the inside of the nose. The nasal volume and the minimal cross-sectional area along the length of the nasal cavity are computed within 10 seconds by a laptop computer equipped with a custom software (Hood Laboratories, Massachussets, U.S.A.). Nasal challenge is delivered directly to the animal's nasal cavity (50 μL volume). The changes in nasal congestion are recorded prior to and for 60–120 minutes post-challenge. If nasal congestion occurs, it will translate into a reduction in the nasal volume.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either PGD2 or *Ascaris suum* antigen; 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of mediator or *Ascaris* antigen response by the test compound. For statistical analysis, paired t-test is used. (References: McFarlane, C. S. et al., Prostaglandins, 28, 173–182 (1984) and McFarlane, C. S. et al., Agents Actions, 22, 63–68 (1987).)

Prevention of Induced Bronchoconstriction in Allergic Sheep

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.); and b) they have previously responded to inhalation challenge with *Ascaris suum* with both an acute bronchoconstriction and a late bronchial obstruction (W. M. Abraham et al., Am. Rev. Resp. Dis., 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

REFERENCE EXAMPLE 1

(1R)-1-[4-(trifluoromethyl)phenyl]ethanol

To (S)-2-methyl-CBS-oxazaborolidine (Callery, 1M in toluene, 1 eq.) at −45° C. was added $BH_3.Me_2S$ (1.06 eq.). This solution was stirred for 10 minutes at −45° C. and then placed in a −30° C. cooling bath before the slow dropwise addition of a 1M dichloromethane solution of 4'-(trifluoromethyl)acetophenone. The reaction mixture was allowed to stir for 214 3 hours at −30° C. After completion of the reaction, excess MeOH was added followed by 1N HCl. After warming up to room temperature, the resulting mixture was filtered through a pad of celite pad eluted with 30% EtOAc in hexane. The organic and aqueous layers were separated and the organic layer was dried over $Na_2SO_4$ and concentrated in vacuo. The resulting oil was purified by flash chromatography (20% EtOAc in hexane) to afford the title compound.

Following the procedures described in Reference Example 1, the following chiral alcohols were prepared from the appropriate ketone:

REFERENCE EXAMPLE 2

(1R)-1-(3,4-dichlorophenyl)ethanol (from 1-(3,4-dichlorophenyl)ethanone)

REFERENCE EXAMPLE 3

(1R)-1-(4-fluorophenyl)ethanol (from 1-(4-fluorophenyl)ethanone)

REFERENCE EXAMPLE 4

(1R)-1-(4-chloro-3-fluorophenyl)ethanol (from 1-(4-chloro-3-fluorophenyl)ethanone, Prepared as Described in Reference Example 9)

REFERENCE EXAMPLE 5

(1R)-1-(3-chlorophenyl)ethanol (from 1-(3-chlorophenyl)ethanone)

REFERENCE EXAMPLE 6

(1R)-1-(4-chloro-2-fluorophenyl)ethanol (from 1-(4-chloro-2-fluorophenyl)ethanone, Prepared as Described in Reference Example 8)

REFERENCE EXAMPLE 7

(1R)-1-(4-bromophenyl)ethanol (from 1-(4-bromophenyl)ethanone)

REFERENCE EXAMPLE 8

1-(4-chloro-2-fluorophenyl)ethanone

To a solution 4-chloro-2-fluorobenzoic acid (1 eq) in $CH_2Cl_2$ (1.6 M) was added N,O-dimethylhydroxylamine hydrochloride (1.5 eq), EDCI (1.5 eq) and triethylamine (4 eq). The reaction mixture was stirred at rt for 16 hrs, concentrated and 0.5M aqueous citric acid was added. The mixture was extracted with 1:1 EtOAc:$Et_2O$. The combined organic layers were washed with brine, dried over $MgSO_4$ and concentrated to give 4-chloro-2-fluoro-N-methoxy-N-methylbenzamide, which was used as such for the next step.

To a solution of the above benzamide (1 eq) in $CH_2Cl_2$ (0.5 M) at 0° C. was added 3M/$Et_2O$ MeMgBr (1.25 eq). The reaction mixture was slowly warmed to rt over a 2 hrs period, quenched with 0.5 M aqueous citric acid and extracted with $Et_2O$. The combined organic layers were washed with brine, dried over $MgSO_4$ and concentrated. The residue was purified by flash chromatography on silica gel eluted with 20% EtOAc/hexane to give the title compound.

REFERENCE EXAMPLE 9

1-(4-chloro-3-fluorophenyl)ethanone

To a solution of 4-chloro-3-fluorobenzaldehyde (1 eq) in THF (0.3 M) at −78° C. was added 3M/$Et_2O$ MeMgBr (1.5 eq). The reaction mixture was stirred at −50° C. for 3 hrs, quenched with aqueous saturated $NH_4Cl$ and extracted with EtOAc. The combined organic layers were dried over $Na_2SO_4$ and concentrated to give 1-(4-chloro-3-fluorophenyl)ethanol, which was used as such for the next step.

To a solution of the above alcohol (1 eq) in $CH_2Cl_2$ (0.3M) at rt was added Dess-Martin periodinane (1.5 eq). The reaction mixture was stirred for 45 minutes at rt and $H_2O$ (10 eq) was added. The mixture was stirred for 30 minutes and filtered through silica gel pad eluted with 30% EtOAc/hexane and concentrated. The residue was purified by flash chromatography on silica gel eluted with 20% EtOAc/hexane to give the title compound.

REFERENCE EXAMPLE 10 methyl[(1R)-6-fluoro-8-(methylsulfonyl)-2,3,4,9-tetrahydro-1H-carbazol-1-yl]acetate

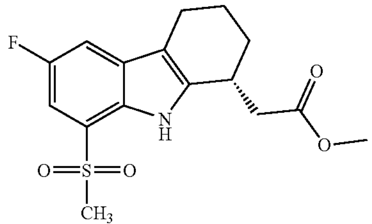

Step 1: 2-(2-bromo-4-fluorophenyl)hydrazinium chloride

To a suspension of 2-bromo-4-fluoroaniline in concentrated HCl (1.5M) at −10° C. was slowly added a 10.0M aqueous solution of $NaNO_2$ (1.1 eq). The mixture was stirred at 0° C. for 2.5 hrs. A cold (−30° C.) solution of $SnCl_2$ (3.8M) in concentrated HCl was then slowly added while maintaining the internal temperature below 10° C. The resulting mixture was stirred mechanically for 20 min at 0, then at room temperature for 1 hr. The thick slurry was filtered and the solid was air dried overnight. The solid was resuspended in cold HCl and filtered again. The dried material was suspended in $Et_2O$, stirred for 10 min, filtered and air dried overnight to give the title compound as a beige solid.

Step 2: (+/−)-ethyl(8-bromo-6-fluoro-2,3,4,9-tetrahydro-1H-carbazol-1-yl)acetate To a suspension of the compound of Step 1 (1 eq) in AcOH (0.5M) was added ethyl(2-oxocyclohexyl)acetate (1 eq). The mixture was stirred at reflux for 16 hrs, cooled and AcOH was removed by evaporation under reduced pressure. The residue was diluted with EtOAc and washed with water and saturated aqueous $NaHCO_3$. The organic layer was dried over $Na_2SO_4$ and concentrated. The residue was then purified on a pad of silica gel, eluting with toluene. The filtrate was concentrated and stirred in hexanes to give, after filtration, the title compound as a white solid. MS (+APCI) m/z 354.2 $(M+H)^+$.

Step 3: (+/−)-ethyl[6-fluoro-8-(methylsulfonyl)-2,3,4,9-tetrahydro-1H-carbazol-1-yl]acetate To a solution of the compound of Step 2 (1 eq) in anhydrous DMSO (0.28M) were added sodium methanesulphinate (3 eq) and copper iodide (3 eq). $N_2$ was bubbled into the mixture for 5 min and the reaction was then stirred at 100° C. under $N_2$ atmosphere. After 12 hrs, more sodium methanesulphinate (2 eq) and copper iodide (2 eq) were added. The mixture was stirred for a further 12 hrs at 100° C., cooled, diluted with EtOAc and 1N HCl was added to acidify the mixture. The suspension was stirred for 30 min and filtered through celite. The filtrate was washed with water, dried over $Na_2SO_4$ and concentrated. The residue was filtered through a pad of silica gel, eluting first with toluene to remove the non-polar impurities and then with a 2:1 mixture of hexanes/EtOAc to elute the desired product. The filtrate from the elution with the mixture of hexanes/EtOAc was concentrated to give the title compound as a pale yellow solid. MS (−APCI) m/z 352.1 $(M-H)^-$.

Step 4: ethyl[(1R)-6-fluoro-8-(methylsulfonyl)-2,3,4,9-tetrahydro-1H-carbazol-1-yl]acetate The racemic mixture from step 3 was resolved by preparative HPLC on a chiralpak AD preparative column eluted with a mixture of 15% iPrOH in hexane. The more polar enantiomer (longer retention time) was identified as the title compound based on the activity of the final product.

Step 5: ethyl[(1R)-9-[(1S)-1-(4-chlorophenyl)ethyl]-6-fluoro-8-(methylsulfonyl)-2,3,4,9-tetrahydro-1H-carbazol-1-yl]acetate To a solution of the compound of Step 4 (1 eq), triphenylphosphine (1.5 eq) and (1R)-1-(4-chlorophenyl)ethanol (1.5 eq, prepared following the general procedure described in Reference Example 1) in THF (0.175M) was added a solution of di-tert-butyl azodicarboxylate (2.1 M in THF, 1.5 eq) over a 10 min period. The mixture was stirred at room temperature for 2 hr and concentrated. The residue was purified by silica gel flash chromatography, eluting with 7% EtOAc in toluene to give the desired product (~90% pure) which was used as such for the next reaction.

Step 6: [(1R)-9-[(1S)-1-(4-chlorophenyl)ethy]-6-fluoro-8-(methylsulfonyl)-2,3,4,9-tetrahydro-1H-carbazol-1-yl]acetic acid and [(1S)-9-[(1S)-1-(4-chlorophenyl)ethyl]-6-fluoro-8-(methylsulfonyl)-2,3,4,9-tetrahydro-1H-carbazol-1-yl]acetic acid To a solution of the compound of Step 5 in a 2:1 mixture of THF and methanol (0.1M) was added 1N aqueous LiOH (3 eq). The mixture was stirred at room temperature for 2 hr, AcOH was added and the solvent was removed by evaporation. The residue was taken up in $EtOAc/H_2O$ and the organic layer was washed with brine, dried over $Na_2SO_4$, filtered and concentrated. The residue was swished in 30% EtOAc in hexane, and the product was suspended in diethyl ether and sonicated for 45 min, filtered, and dried under high vacuum at 50° C. for 24 hr to give the title compound as a white solid. MS (−APCI) m/z 462.1 $(M-H)^-$.

Alternatively (+/−) ethyl[6-fluoro-8-(methylsulfonyl)-2,3,4,9-tetrahydro-1H-carbazol-1-yl]acetate was used for the alkylation reaction in step 5 to give a mixture of 2 diastereomers: ethyl[(1R)-9-[(1S)-1-(4-chlorophenyl)ethyl]-6-fluoro-8-(methylsulfonyl)-2,3,4,9-tetrahydro-1H-carbazol-1-yl]acetate and ethyl[(1S)-9-[(1S)-1-(4-chlorophenyl)ethyl]-6-fluoro-8-(methylsulfonyl)-2,3,4,9-tetrahydro-1H-carbazol-1-yl]acetate. The diastereomeric mixture was resolved by selective hydrolysis using the following procedure to give the desired [(1R)-9-[(1S)-1-(4-chlorophenyl)ethyl]-6-fluoro-8-(methylsulfonyl)-2,3,4,9-tetrahydro-1H-carbazol-1-yl]acetic acid.

Resolution:

The diastereomeric mixture of ethyl[(1R)-9-[(1S)-1-(4-chlorophenyl)ethyl]-6-fluoro-8-(methylsulfonyl)-2,3,4,9-tetrahydro-1H-carbazol-1-yl]acetate and ethyl[(1S)-9-[(1S)-1-(4-chlorophenyl)-ethyl]-6-fluoro-8-(methylsulfonyl)-2,3, 4,9-tetrahydro-1H-carbazol-1-yl]acetate (1 eq) was dissolved in a 3.5/1 mixture of THF/MeOH (0.25M) and cooled at 0° C. Aqueous LiOH 1N (1 eq) was slowly added and the mixture was stirred at 0° C. for 12 h or until almost complete hydrolysis of ethyl[(1R)-9-[(1S)-1-(4-chlorophenyl)ethyl]-6-fluoro-8-(methylsulfonyl)-2,3,4,9-tetrahydro-1H-carbazol-1-yl]acetate, the other diastereomer was only slightly hydrolyzed under these conditions. AcOH was added and the solvent was removed by evaporation. The residue was taken up in EtOAc/$H_2O$ and the organic layer was washed with brine, dried over $Na_2SO_4$, filtered and concentrated. Ethyl[(1S)-9-[(1S)-1-(4-chlorophenyl)ethyl]-6-fluoro-8-(methylsulfonyl)-2,3,4,9-tetrahydro-1H-carbazol-1-yl]acetate and [(1R)-9-[(1S)-1-(4-chloro-phenyl)ethyl]-6-fluoro-8-(methylsulfonyl)-2,3,4,9-tetrahydro-1H-carbazol-1-yl]acetic acid were separated by flash chromatography eluting with 40% EtOAc in hexanes containing 1% AcOH to give the desired [(1R)-9-[(1S)-1-(4-chlorophenyl)ethyl]-6-fluoro-8-(methylsulfonyl)-2,3,4,9-tetrahydro-1H-carbazol-1-yl]acetic acid with de>90% which was swished in 30% EtOAc in hexane to give the desired compound as a white solid with de>95%.

Step 7: methyl[(1R)-6-fluoro-8-(methylsulfonyl)-2,3,4,9-tetrahydro-1H-carbazol-1-yl]acetate To a solution of [(1R)-9-[(1S)-1-(4-chlorophenyl)ethyl]-6-fluoro-8-(methylsulfonyl)-2,3,4,9-tetrahydro-1H-carbazol-1-yl]acetic acid ($[\alpha]_D$=−226° in MeOH) in MeOH (0.1M) was added 10% palladium on carbon (10% wt/wt). A stream of $N_2$ was bubbled through the mixture for 5 min. The reaction was stirred at rt under $H_2$ atmosphere (balloon) for 24 hrs and filtered through a celite pad eluted with $CH_2Cl_2$. The solvents were removed by evaporation under reduced pressure and the residue was swished in MeOH to give the title compound.

The following examples are provided to illustrate the invention and are not to be construed as limiting the scope thereof in any manner.

EXAMPLE 1

((1R)-6-fluoro-8-(methylsulfonyl)-9-{(1S)-1-[4-(trifluoromethyl)phenyl]ethyl}-2,3,4,9-tetrahydro-1H-carbazol-1-yl)acetic acid

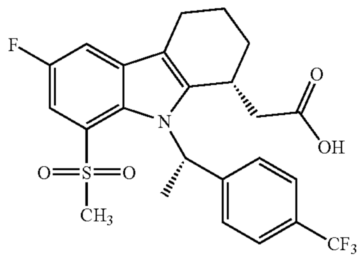

To a solution of the compound of Reference Example 10 (1 eq), triphenylphosphine (1.5 eq) and (1R)-1-[4-(trifluoromethyl)phenyl]ethanol (1.5 eq) in THF (0.2M) was added a solution of di-tert-butyl azodicarboxylate (1M in THF, 1.5 eq) over a 20 min period. The mixture was stirred at room temperature for 2 hr and concentrated. The residue was purified by silica gel flash chromatography eluted with 10% EtOAc in toluene to give methyl((1R)-6-fluoro-8-(methylsulfonyl)-9-{(1S)-1-[4-(trifluoro-methyl)phenyl]ethyl}-2,3,4,9-tetrahydro-1H-carbazol-1-yl)acetate (90% pure) which was used as such for the next reaction.

To a solution of the above ester (1 eq) in a 3.5/1 mixture of THF/MeOH (0.25M) at 0° C. was slowly added aqueous LiOH 1N (1 eq) and the mixture was stirred at 0° C. for 16 h or until almost complete hydrolysis of the ester; under these conditions, the other minor diastereomer has a much slower rate of hydrolysis. AcOH was added and the solvent was removed in vacuo. The residue was taken up in EtOAc/$H_2O$ and the organic layer was washed with brine, dried over $Na_2SO_4$ filtered and concentrated. To remove the unreacted methyl ester, the residue was filtered through a pad of silica gel eluting first with 10% EtOAc/toluene and then with 60% EtOAc/toluene containing 1% of AcOH. The residue was swished in 30% EtOAc/hexane and dried under high vacuum at 50° C. for 16 hr to give the desired title compound as a white solid with de and ee >95% (checked by chiral HPLC). MS (−APCI) m/z 496.0 $(M-H)^-$. $[\alpha]_D$=−181° in MeOH.

The procedures described in Example 1 were followed using compound of Reference Example 10 and the appropriate alcohols, to provide the compounds listed below following hydrolysis of their corresponding methyl esters:

EXAMPLE 2

[(1R)-9-[(1S)-1-(3,4-dichlorophenyl)ethyl]-6-fluoro-8-(methylsulfonyl)-2,3,4,9-tetrahydro-1H-carbazol-1-yl]acetic acid starting from (1R)-1-(3,4-dichlorophenyl)ethanol. MS (−APCI) m/z 495.9 $(M-H)^-$. $[\alpha]_D$=−220° in MeOH.

EXAMPLE 3

{(1R)-6-fluoro-8-(methylsulfonyl)-9-[(1S)-1-phenylethyl]-2,3,4,9-tetrahydro-1H-carbazol-1-yl}acetic acid starting from commercially available (1R)-1-phenylethanol. MS (−APCI) m/z 427.9 $(M-H)^-$. $[\alpha]_D$=−178° in MeOH

EXAMPLE 4

[(1R)-6-fluoro-9-[(1S)-1-(4-fluorophenyl)ethyl]-8-(methylsulfonyl)-2,3,4,9-tetrahydro-1H-carbazol-1-yl]acetic acid starting from (1R)-1-(4-fluorophenyl)ethanol. MS (−APCI) m/z 446.0 $(M-H)^-$. $[\alpha]_D$=−174° in MeOH.

EXAMPLE 5

[(1R)-9-[(1S)-1-(4-chloro-3-fluorophenyl)ethyl]-6-fluoro-8-(methylsulfonyl)-2,3,4,9-tetrahydro-1H-carbazol-1-yl]acetic acid starting from (1R)-1-(4-chloro-3-fluorophenyl)ethanol. MS (−APCI) m/z 480.1 $(M-H)^-$. $[\alpha]_D$=−211° in MeOH.

EXAMPLE 6

[(1R)-9-[(1S)-1-(3-chlorophenyl)ethyl]-6-fluoro-8-(methylsulfonyl)-2,3,4,9-tetrahydro-1H-carbazol-1-yl]acetic acid starting from (1R)-1-(3-chlorophenyl)ethanol. MS (+APCI) m/z 464.0 $(M+H)^+$. $[\alpha]_D$=−192°in MeOH

EXAMPLE 7

[(1R)-9-[(1S)-1-(4-chloro-2-fluorophenyl)ethyl]-6-fluoro-8-(methylsulfonyl)-2,3,4,9-tetrahydro-1H-carbazol-1-yl]acetic acid starting from (1R)-1-(4-chloro-2-fluorophenyl)ethanol. MS (−APCI) m/z 480.1 $(M-H)^-$. $[\alpha]_D$=−250° in MeOH

EXAMPLE 8

[(1R)-9-[(1S)-1-(4-bromophenyl)ethyl]-6-fluoro-8-(methylsulfonyl)-2,3,4,9-tetrahydro-1H-carbazol-1-yl]acetic acid starting from (1R)-1-(4-bromophenyl)ethanol. MS (−APCI) m/z 506.1 $(M-H)^-$. $[\alpha]_D$=−217° in MeOH

EXAMPLE 9

[(1R)-9-[(1S)-1-(4-cyanophenyl)ethyl]-6-fluoro-8-(methylsulfonyl)-2,3,4,9-tetrahydro-1H-carbazol-1-yl]acetic acid

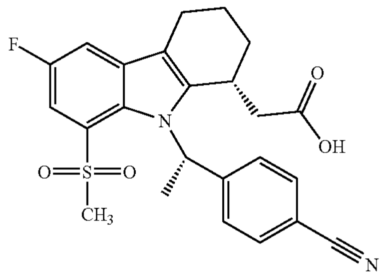

To a solution of the methyl ester of compound of Example 8 (1 eq) in DMF (0.08 M) was added 1,1'-bis(diphenylphosphino)ferrocene (0.05 eq), tris(dibenzylideneacetone)dipalladium(0) (0.05 eq), zinc cyanide (2.5 eq) and $H_2O$ (10 eq). The mixture was degassed and stirred under nitrogen at 90° C. for 16 hrs, cooled to rt and 1N HCl was added. The reaction mixture was extracted with EtOAc and the combined organic layers were washed with brine, dried over $Na_2SO_4$ and concentrated. The residue was purified by flash chromatography on silica gel eluted with gradient from 20% EtOAc/hexane to 50% EtOAc/hexane to give methyl[(1R)-9-[(1S)-1-(4-cyanophenyl)ethyl]-6-fluoro-8-(methylsulfonyl)-2,3,4,9-tetrahydro-1H-carbazol-1-yl]acetate which, upon hydrolysis as described in Example 1, provided the title compound. MS (−APCI) m/z 453.1 $(M-H)^-$. $[\alpha]_D$=248° in MeOH

EXAMPLE 10

((1R)-6-fluoro-8-(methylsulfonyl)-9-{(1S)-1-[4-(methylsulfonyl)phenyl]ethyl}-2,3,4,9-tetrahydro-1H-carbazol 1-yl)acetic acid

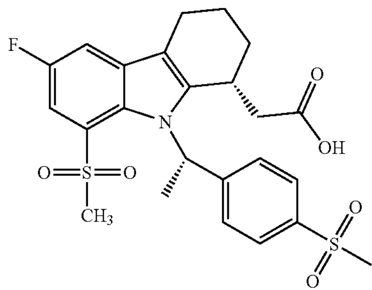

To a solution of the methyl ester of compound of Example 8 (1 eq) in DMSO (0.1 M) was added methanesulfinic acid sodium salt (3 eq) and copper(I) iodide (3 eq). The mixture was degassed and stirred under nitrogen at 110° C. for 16 hrs, cooled to rt and EtOAc and aqueous saturated $NH_4Cl$ were added. The reaction mixture was extracted with EtOAc and the combined organic layers were washed with brine, dried over $Na_2SO_4$ and concentrated. The residue was purified by flash chromatography on silica gel eluted with gradient from 20% EtOAc/hexane to 50% EtOAc/hexane to give methyl((1R)-6-fluoro-8-(methylsulfonyl)-9-{(1S)-1-[4-(methylsulfonyl)phenyl]ethyl}-2,3,4,9-tetrahydro-1H-carbazol-1-yl)acetate which, upon hydrolysis as described in Example 1, provided the title compound. MS (−APCI) m/z 506.1 $(M-H)^-$ $[\alpha]_D$=−208° in MeOH.

EXAMPLE 11

((1R)-6-fluoro-8-(methylsulfonyl)-4-oxo-9-{(1S)-1-[4-(trifluoromethyl)phenyl]ethyl}-2,3,4,9-tetrahydro-1H-carbazol-1-yl)acetic acid

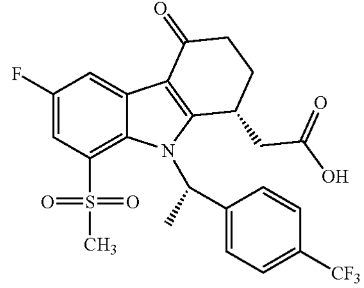

Step 1: methyl[(1R)-6-fluoro-8-(methylsulfonyl)$_4$-oxo-2,3,4,9-tetrahydro-1H-carbazol-1-yl]acetate To a solution of the compound of Reference Example 10 (1 eq) in THF/$H_2O$ (15:1, 0.1 M) was added DDQ (5 eq). The mixture was stirred for 16 hrs at rt, diluted with EtOAc and washed with aqueous saturated $NaHCO_3$. The organic layer was washed with brine, dried over $Na_2SO_4$ and concentrated and the residue was used as such for the next step.

Step 2: ((1R)-6-fluoro-8-(methylsulfonyl)-4-oxo-9-{(1S)-1-[4-(trifluoromethyl)phenyl]ethyl}-2,3,4,9-tetrahydro-1H-carbazol-1-yl)acetic acid The procedures described in Example 1 were followed using compound of Step 1 and (1R)-1-[4-(trifluoromethyl)phenyl]ethanol to provide the title compound following the hydrolysis of the corresponding methyl ester. MS (+APCI) m/z 511.9 $(M)^+$

EXAMPLE 12

((1R,4R)-6-fluoro-4-hydroxy-8-(methylsulfonyl)-9-{(1S)-1-[4-(trifluoromethyl)phenyl]ethyl}-2,3,4,9-tetrahydro-1H-carbazol-1-yl)acetic acid

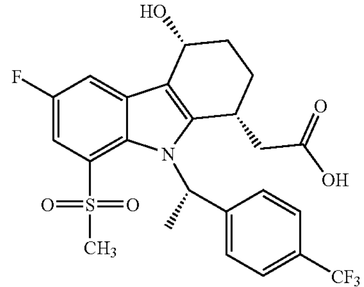

Step 1: methyl[1R)-6-fluoro-4-hydroxy-8-(methylsulfonyl)-2,3,4,9-tetrahydro-1H-carbazol-1-yl]acetate To a solution of the compound of Reference Example 10 (1 eq) in AcOH/Toluene (1:1, 0.2 M) was added DDQ (1 eq). The mixture was stirred for 2 hrs at rt and quenched with aqueous saturated $NaHCO_3$ and then extracted with EtOAc. The organic layer was washed with brine, dried over $Na_2SO_4$ and concentrated. The residue was purified by flash chromatography on silica gel eluted with 10–50% EtOAc/hexanes to afford the title compound.

Step 2: ((1R,4R)-6-fluoro-4-hydroxy-8-(methylsulfonyl)-9-{(1S)-1-[4-(trifluoromethyl)phenyl]ethyl}-2,3,4,9-tetrahydro-1H-carbazol-1-yl)acetic acid To a solution of the compound of Step 1 (1 eq), triphenylphosphine (1.5 eq) and (1R)-1-[4-(trifluoromethyl)phenyl]ethanol (1.5 eq) in THF (0.2M) was added di-tert-butyl azodicarboxylate (1M in THF, 1.5 eq). The mixture was heated in microwave at 150° C. under normal intensity for 5 min. cooled to rt and 1.5 eq of the alcohol, triphenylphosphine and di-tert-butyl azodicarboxylate were added. The mixture was heated in microwave for a further 5 min at 150° C. at normal intensity and cooled to rt. The solvent was removed and the residue was purified by silica gel flash chromatography eluted with 10%–60% EtOAc/hexanes to afford two isomers. The less polar isomer was identified as methyl((1R,4R)-6-fluoro-4-hydroxy-8-(methylsulfonyl)-9-{(1S)-1-[4-(trifluoromethyl)phenyl]ethyl}-2,3,4,9-tetrahydro-1H-carbazol-1-yl)acetate and the more polar isomer as methyl((1R,4S)-6-fluoro-4-hydroxy-8-(methylsulfonyl)-9-{(1S)-1-[4-(trifluoromethyl)phenyl]ethyl}-2,3,4,9-tetrahydro-1H-carbazol-1-yl)acetate. To a solution of methyl((1R, 4R)-6-fluoro-4-hydroxy-8-(methylsulfonyl)-9-{(1S)-1-[4-(trifluoromethyl)phenyl]ethyl}-2,3,4,9-tetrahydro-1H-carbazol-1-yl)acetate (1 eq) in a 3.5/1 mixture of THF/MeOH (0.25M) at 0° C. was slowly added aqueous 1N LiOH (1 eq) and the mixture was stirred at rt for 2 h. 1M pH 7.4 phosphate buffer was added followed by addition of EtOAc and brine to the mixture. The aqueous layer was extracted with EtOAc and the combined organic layers were dried over $Na_2SO_4$, filtered and concentrated to afford the title compound. MS (−APCI) m/z 511.9 $(M-H)^-$.

EXAMPLE 13

((1R,4S)-6-fluoro-4-hydroxy-8-(methylsulfonyl)-9-{(1S)-1-[4-(trifluoromethyl)phenyl]ethyl}-2,3,4,9-tetrahydro-1H-carbazol-1-yl)acetic acid

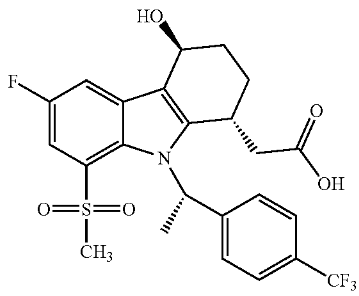

The title compound was prepared by hydrolysis of methyl ((1R,4S)-6-fluoro-4-hydroxy-8-(methylsulfonyl)-9-{((1S)-1-[4-(trifluoromethyl)phenyl]ethyl}-2,3,4,9-tetrahydro-1H-carbazol-1-yl)acetate from Example 12 Step 2 (more polar isomer) by following the hydrolysis procedure described in Example 12 Step 2. MS (−APCI) m/z 512.0 $(M-H)^-$.

What is claimed is:

1. A compound of the formula I:

I

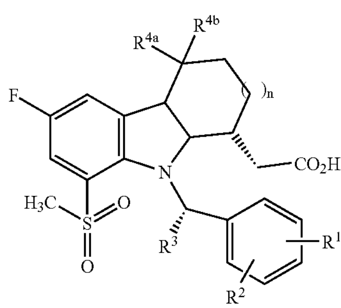

and pharmaceutically acceptable salts thereof, wherein n is 0 or 1; $R^1$ is hydrogen or halogen; $R^2$ is halogen, cyano, $C_{1-3}$alkylsulfonyl or trifluoromethyl; and $R^3$ is $C_{1-3}$alkyl optionally substituted with 1–5 halogen atoms; and $R^{4a}$ and $R^{4b}$ are each hydrogen or one is hydrogen and the other is hydroxy, or both together represent oxo; with the proviso that when $R^1$ is hydrogen, $R^2$ is not 4-chloro.

2. A compound of claim 1 wherein $R^{4a}$ and $R^{4b}$ are each hydrogen.

3. A compound of claim 1 wherein $R^1$ is hydrogen and $R^2$ is $CF_3$.

4. A compound of claim 1 wherein $R^3$ is $CH_3$.

5. A compound of claim 1 wherein $R^1$ and $R^2$ are independently a halogen atom.

6. A compound of claim 1 wherein n is 1.

7. A compound of claim 1 wherein n is 1, $R^3$ is $CH_3$, and $R^{4a}$ and $R^{4b}$ are each hydrogen.

8. A compound of claim 7 wherein $R^1$ is hydrogen and $R^2$ is $CF_3$.

9. A compound of claim 1 selected from:

((1R)-6-fluoro-8-(methylsulfonyl)-9-{(1S)-1-[4-(trifluoromethyl)phenyl]ethyl}-2,3,4,9-tetrahydro-1H-carbazol-1-yl)acetic acid;

[(1R)-9-[(1S)-1-(3,4-dichlorophenyl)ethyl]-6-fluoro-8-(methylsulfonyl)-2,3,4,9-tetrahydro-1H-carbazol-1-yl] acetic acid;

{(1R)-6-fluoro-8-(methylsulfonyl)-9-[(1S)-1-phenylethyl]-2,3,4,9-tetrahydro-1H-carbazol-1-yl}acid;

[(1R)-6-fluoro-9-[(1S)-1-(4-fluorophenyl)ethyl]-8-(methylsulfonyl)-2,3,4,9-tetrahydro-1H-carbazol-1-yl]acetic acid;

[(1R)-9-[(1S)-1(4-chloro-3-fluorophenyl)ethyl]-6-fluoro-8-(methylsulfonyl)-2,3,4,9-tetrahydro-1H-carbazol-1-yl]acetic acid;

[(1R)-9-[(1S)-1-(3-chlorophenyl)ethyl]-6-fluoro-8-(methylsulfonyl)-2,3,4,9-tetrahydro-1H-carbazol-1-yl]acetic acid;

[(1R)-9-[(1S)-1-(4-chloro-2-fluorophenyl)ethyl]-6-fluoro-8-(methylsulfonyl)-2,3,4,9-tetrahydro-1H-carbazol-1-yl]acetic acid;

[(1R)-9-[(1S)-1-(4-bromophenyl)ethyl]-6-fluoro-8-(methylsulfonyl)-2,3,4,9-tetrahydro-1H-carbazol-1-yl]acetic acid;

[(1R)-9-[(1S)-1-(4-cyanophenyl)ethyl]-6-fluoro-8-(methylsulfonyl)-2,3,4,9-tetrahydro-1H-carbazol-1-yl]acetic acid; and ((1R)-6-fluoro-8-(methylsulfonyl)-9-{(1S)-1-[4-(methylsulfonyl)phenyl]ethyl}-2,3,4,9-tetrahydro-1H-carbazol-1-yl)acetic acid; and pharmaceutically acceptable salts therof.

10. A pharmaceutical composition comprising a compound of claim 1 and a pharmaceutically acceptable carrier.

11. A method for the treatment rhinitis, asthma, or nasal congestion which comprises administering to a patient a therapeutically effective amount of a compound of claim 1.

* * * * *